United States Patent [19]
Abercrombie

[11] Patent Number: 5,845,653
[45] Date of Patent: Dec. 8, 1998

[54] APPLICATOR FOR COLORING HAIR OR FIBERS AND METHODS FOR MAKING AND USING SAME

[76] Inventor: Tracy H. Abercrombie, 1229 1/2 Smithwood Dr., Los Angeles, Calif. 90035

[21] Appl. No.: 79,751

[22] Filed: May 15, 1998

[51] Int. Cl.⁶ .............................. A61K 7/13; A61K 7/135
[52] U.S. Cl. ..................... 132/208; 132/207; 132/108; 424/73; 521/52; 15/104.94
[58] Field of Search ................... 132/202, 200, 132/208, 207, 222, 270, 109, 212, 108, 110; 521/52; 424/73; 15/104.94, 244.1, 118, 223

[56] References Cited

U.S. PATENT DOCUMENTS

| | | | |
|---|---|---|---|
| 2,705,499 | 4/1955 | Breeze | 132/109 |
| 3,262,459 | 7/1966 | Sheehan | 132/108 |
| 3,570,036 | 3/1971 | Gilchrist et al. | 15/104.94 |
| 4,793,019 | 12/1988 | Stima et al. | 15/104.94 |
| 5,044,383 | 9/1991 | Alessio et al. | 132/320 |
| 5,261,426 | 11/1993 | Kellett et al. | 132/108 |

Primary Examiner—Cary E. O'Connor
Assistant Examiner—Pedro Philogene
Attorney, Agent, or Firm—Albert O. Cota

[57] ABSTRACT

An applicator (10) for transferring color-altering material from a rigid substrate (12) to hair or fibers, and methods for making and using the same. The applicator (10) includes a first side (14) and a second side (16). A color-altering dye material (38), which is soluble in water and water-activated, is affixed to at least one of the sides (14,16) of the applicator (10). The applicator (10) is made of a material such as plastic (26), wood (28) or metal (30) and includes a handle (102) for grasping and manipulating the applicator (10) during use. The color of the dye material (38) can be the same, different, or a combination thereof. Use of the applicator (10) requires wetting the hair or fibers, and then wiping the water-activated color-altering material (38) against the hair or fibers.

40 Claims, 3 Drawing Sheets

APPLICATOR FOR COLORING HAIR OR FIBERS AND METHODS FOR MAKING AND USING SAME

TECHNICAL FIELD

The present invention pertains in general to devices and methods for coloring hair or fibers, and more particularly to an applicator for applying coloring material to hairs on the body or fibers in textile materials.

BACKGROUND ART

Apparatuses and methods for applying color-altering materials, such as dyes, to hair or fibers for the purpose of temporarily or permanently changing the color is well-known in the prior art. In the case of hair, such as human hair, the purpose typically is to cover unsightly or undesired indicators of aging. In the case of fibers, such as textile fibers, the purpose might be to cover stains or to resurrect old and faded products.

Typically, the color of hair or fibers can be altered through the use of rinses, sprays, lotions or creams. When darkening hair, the coloring material usually takes the form of a dye; when lightening hair, a bleach and activator combination, along with a toner is utilized. Regardless of the coloring material that is used, they are applied in a step-by-step manner, often requiring a waiting period to allow the chemicals in the coloring material to react and for the materials to bond with the hair.

Against this background of known technology, the applicants have developed a new, more efficient, and speedier applicator for applying coloring material to hair or fibers which can be performed in or outside the confines of a hair salon or a textile factory.

More particularly, the invention discloses a dye-bearing rigid applicator and a method for using such. The applicator is constructed in such a manner as to enable the transfer of dye material to the hair or fibers without requiring the user to mix or touch the dye or other chemicals carried by the substrate.

A search of the prior art did not disclose any patents that read directly on the claims of the instant invention, however the following U.S. patents are considered related:

| U.S. PAT. NO. | INVENTOR | ISSUED |
|---|---|---|
| 5,146,937 | Lefebvre | 15 September 1992 |
| 5,002,075 | Kellett et al | 26 March 1991 |
| 4,271,272 | Strickman et al | 2 June 1981 |
| 4,206,195 | Bolich, Jr. et al | 3 June 1980 |

The U.S. Pat. No. 5,146,937 to Lefebvre discloses the use of a sheet made of a polymer material having semi-flexible, thermally-insulating, hair-clinging, non-porous, non-slipping properties, as a dye-applying pad for hair highlighting. The polystyrene sheet defines one and another opposite flat portions merging about a fold line. A lock of hair is laid over one flat half portion of the sheet, and a fluid dye solution is applied to the lock of hair. The other flat half portion of the sheet is then folded over and flatly compressed against the first portion of sheet to take the locks in sandwich for a sufficient development time to enable permanent hair coloring.

The U.S. Pat. No. 5,002,075 to Kellett, et al discloses a hair conditioning and styling pad which comprises a shaped body of a resilient, open-celled, hydrophilic polyurethane foam matrix integrally incorporating an aqueous phase incorporating about 70–90% water, about 5–25% of a hair conditioning agent, and a nonionic surfactant. The pad is preferably affixed to the tines of a styling brush or comb to yield a composite brush or comb which is effective to condition and style hair. In a further modification of the invention, color-modified aqueous phases further comprise about 5–25% of a temporary hair coloring agent, and the percentage of water in the color-modified aqueous phase will be about 60–80%.

The U.S. Pat. No. 4,271,272 to Strickman, et al discloses synthetic polyurethane sponges manufactured with at least four percent of one or more additives dispersed therein. The additives may be soap, lotions, detergents, pesticides, lanolin, scouring particles, silicone coils, bath oils, or the like or combinations thereof. The sponges' skeletons are developed by reaction of a polyether or a polyester with a suitable isocyanate in the presence of a catalyst with the additives entrapped in the voids of the sponges. An additive-bearing material, containing the additive is prepared and is then mixed into a foam-forming reaction mass.

The U.S. Pat. No. 4,206,195 to Bolich, Jr., et al discloses an article especially designed for conditioning hair. The article is comprised of a flexible substrate releasably carrying a hair conditioning agent and a water soluble salt. The article when rubbed onto hair provides combing, detangling, static fly-away and softness benefits. Additionally, the manageability of the hair is improved.

For background purposes and as indicative of the art to which the invention is related reference may be made to the remaining cited patents.

| U.S. PAT. NO. | INVENTOR | ISSUED |
|---|---|---|
| 5,121,762 | Dipinto, et al | 16 June 1992 |
| 4,658,839 | Dallal, et al | 21 April 1987 |
| 4,594,362 | Smith, et al | 10 June 1986 |
| 2,140,682A (U.K.) | Sanders | 5 December 1984 |
| 4,344,930 | MacRae, et al | 17 August 1982 |
| 2,299,985 | Hudson | 27 October 1942 |

DISCLOSURE OF THE INVENTION

The present invention discloses an applicator and a method for transferring color-altering material to strands of hair or fibers. In its most basic design, the applicator is comprised of:

a) a rigid substrate having a first side, a second side, an outer edge, an inner edge, an upper edge and a lower edge.

b) a means for affixing a water-activated color-altering material to at least one side of said rigid substrate, and c) a means for grasping and manipulating the rigid substrate.

In view of the above, it is the primary object of the invention to provide a hair or fiber color applicator to which is affixed a water-activated color-altering dye, and a method for making and using the applicator, while overcoming many drawbacks and disadvantages of other color applicators known in the art.

Another object of the invention is to provide novel methods for securing the water-activated color-altering dye on a thin, rigid substrate. The dye is adhered to at least one side of the substrate in a predetermined pattern or configuration.

Still another object of the invention is to provide an applicator for transferring the dye from one surface to another, where the one surface consists of a rigid substrate to which the dye is affixed and the other surface consists of the exterior of fibers, such as human hair or textiles. The material for the rigid substrate can consist of a thin, flat sheet of plastic, wood or a metal. The substrate can be designed to include an outward extending handle or a second rigid substrate which is secured to the first substrate by means of a living hinge. In either design, the applicator is comfortable and easily manipulated when held in a human hand.

In the second design, the dye or colorant is applied to the interfacing inner sides of the two substrates. To use the second design, the hair or fibers are placed between the two substrates. The outer sides are then grasped, squeezed and moved along the hair or fibers. As the applicator is moved, the colorant is transferred to the hair or fibers.

Yet another object of the invention is to provide a plurality of applicator designs wherein each design comprises a rigid substrate conformable to a human hand wherein on one or both sides of the substrate is affixed a dye material.

Use of an applicator involves either wetting a bundle of hair or fibers to be colored, or wetting the surface of the substrate containing the dye, or wetting both the hair/fiber and the substrate and contacting the dye-containing portion of the substrate with the surface to be colored. In one embodiment, for example when touching up the rootline of the hair, the dye-containing portion of the substrate is simply rubbed against the root area to be colored. In an alternate embodiment, if it is desired to cover the entire surface of a hair or fiber bundle, the user wipes the substrate about the bundle of hair or fibers.

In addition to the above objects of the invention it is also an object of the invention to provide an applicator that:

- allows two or more of the applicators to be packaged together as a set or a kit with the dye colorant on the applicator being the same, different, or a combination thereof,
- can be made in a variety of rigid materials,
- allows a large spectrum of dye colorants to be applied,
- has a long shelf life, and
- is cost effective from both a consumer and a manufacturer point of view.

These and other objects and advantages of the present invention will become apparent from the subsequent detailed description of the preferred embodiment and the appended claims taken in conjunction with the accompanying drawings.

BEST MODE FOR CARRYING OUT THE INVENTION

The best mode for carrying out the invention is presented in terms of a preferred embodiment for a rigid applicator that has affixed a water-activated color-altering material and a method for transferring the material to strands of hair or fibers. The preferred embodiment, as shown in FIGS. 1–12, consists of an applicator 10 which is comprised of the following major elements: a rigid substrate 12, a water-activated color-altering material 38, a flexible substrate 60 and a means for grasping the rigid substrate 12.

Figure 7:
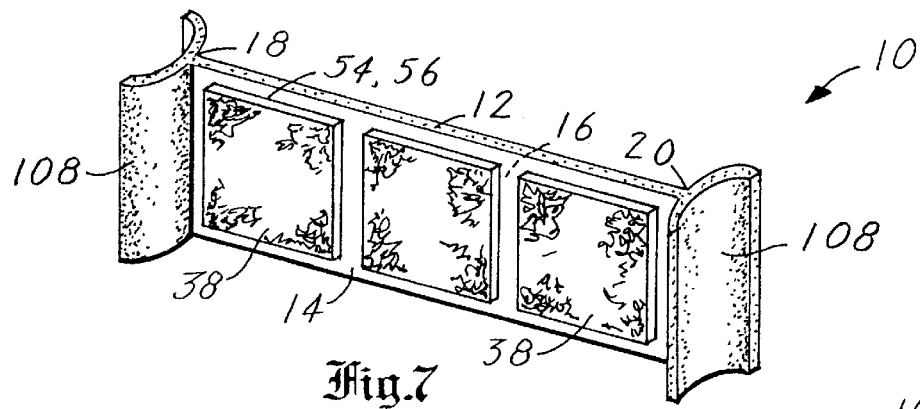
FIG. 7 is a perspective view of a flexible substrate that has a finger slot located on the outer and inner edges of the rigid substrate.
Figure 8:
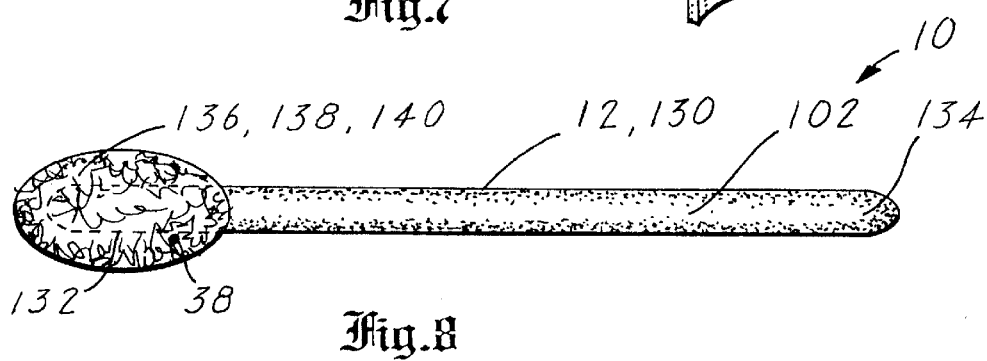
FIG. 8 is an elevational side view of an applicator having a rigid substrate with a front section that includes a bundle of soft fibers.
Figure 9:
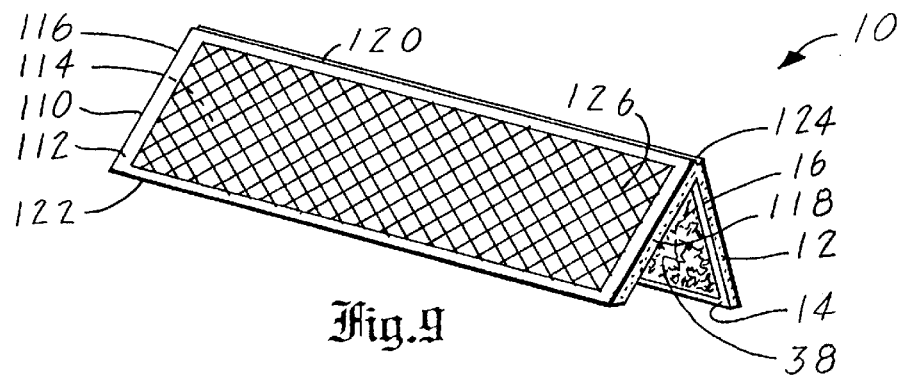
FIG. 9 is a perspective view of an applicator which includes a pair of rigid substrate that are joined at their upper edges by a living hinge. The first sides include the water-activated color-altering material and the second sides are used to grip the applicator during usage.
Figure 10:
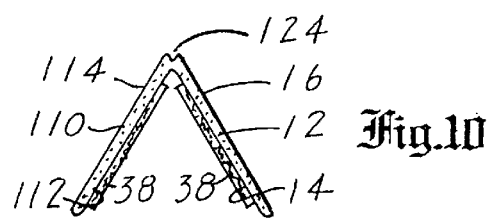
FIG. 10 is a front elevational view of the applicator described in FIG. 10.

The rigid substrate 12 which functions as the applicator 10 can be configured as a single-plane unit as shown in FIGS. 1–8 or in a double-substrate configuration as shown in FIGS. 9 and 10.

The single plane unit of the rigid substrate 12 as shown in FIGS. 1, 2, 3, 6 and 7, includes a first side 14, a second side 16, an outer edge 18, an inner edge 20, an upper edge 22 and a lower edge 24. The substrate 12 includes a means 36 for affixing the water-activated color-altering material 38 to at least one of the sides 14,16 of the substrate 12. The substrate also includes a means 100 for grasping and manipulating the rigid substrate during usage. The rigid substrate 12 can be made from a plastic material 26, a wood 28 or a metal 30 with a plastic such as polyvinylchloride, polyethylene or polycarbonate preferred.

In FIG. 8 is shown a modified single plane unit wherein the rigid substrate 12 is comprised of an elongated narrow structure 130 having a front section 132 and a rear section 134. Around the front section 132 is attached a bundle of soft fibers 136 consisting of cotton fibers 138, sponge fibers 140 or the like. To the soft fibers 136 is affixed the water-activated color-altering material 38. The rear section 134 of the structure 130 extending from the bundle of soft fibers 136, functions as a handle 102 which provides the means by which the applicator 10 is grasped and manipulated.

The departure from the single-plane applicator is shown in FIGS. 9 and 10. In this design, the rigid substrate 12 is paired with a second rigid substrate 110 having similar dimensions as the rigid substrate 12. The second rigid substrate also has a first side 112, a second side 114, an outer edge 116, an inner edge 118, an upper edge 120 and a lower edge 122. The upper edge 120 of the second rigid substrate 110 is attached, by means of a living hinge 124, to the upper edge 22 of the rigid substrate 12. To at least one of the first sides of the rigid substrate or the second rigid substrate is affixed the water-activated color-altering material 38. The second sides 16,114 provide the means by which the applicator 10 is grasped and manipulated during usage. As shown in FIG. 9, the surfaces of the second sides 16,114 may include a serrated gripping surface 126.

Figure 2:
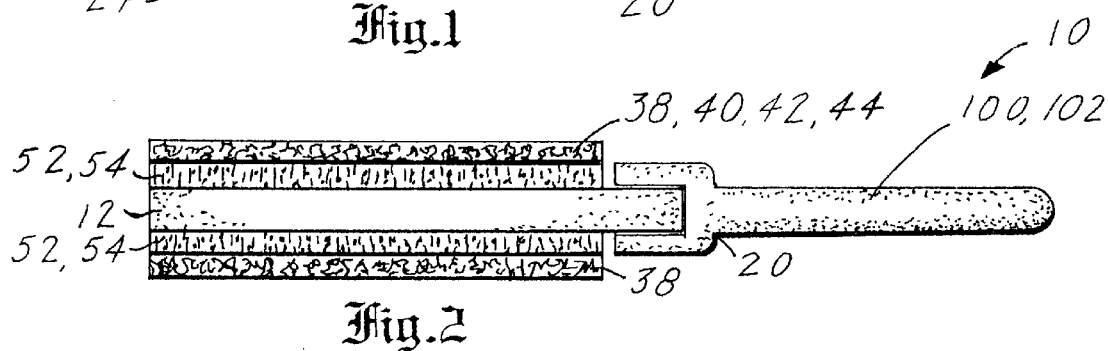
FIG. 2 is a top plan view of an applicator having a handle with a slot that is inserted into the inner edge of the rigid substrate.

The water-activated color-altering material 38 can be formulated to include one or more of a hair color 40, a bleaching compound 42 and a conditioning agent 44 as shown in FIG. 2. The material 38 can also be formulated with a hair color that is permanent 46, semi-permanent 48 or demi-permanent 50 as shown in FIG. 3.

Figure 6:
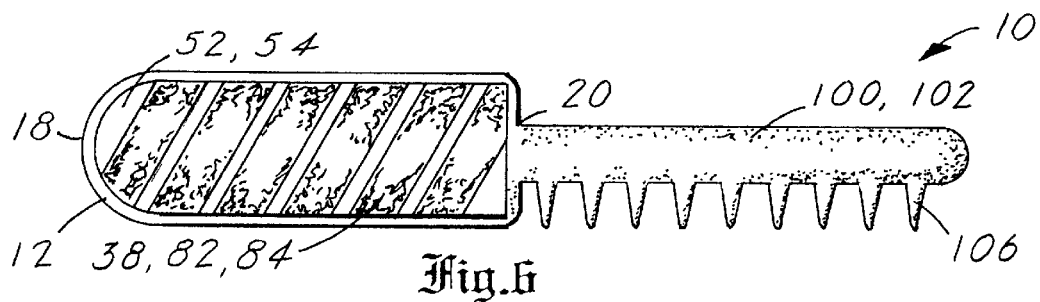
FIG. 6 is an elevational side view of an applicator having a handle that includes a plurality of combing teeth.

The means 36 for affixing the water-activated color-altering material 38 comprises a water soluble binder material 52. The material 52 incorporates an adhesive 54 which allows the material 52 to be directly affixed to at least one Of the sides 14 or 16 of the rigid substrate 12 as shown in FIG. 2. The color-altering material 38 is then directly affixed to the binder material 52. The binder material 52, the adhesive 54 and the color-altering material 38 are all water soluble. The color-altering material 38 is preferably a dry particulate 82 or a powder 84. The binder material 52 functions as an adhesive 54 to secure the particulate 82 or the powder 84 to at least one of sides 14,16 of the rigid substrate 12 as shown in FIG. 6.

In addition to the direct application of the water-activated color-altering material 38 to the rigid substrate 12, a second means 36 for affixing the color-altering material 38 which utilizes the separate flexible substrate 60 may be utilized.

Figure 3:
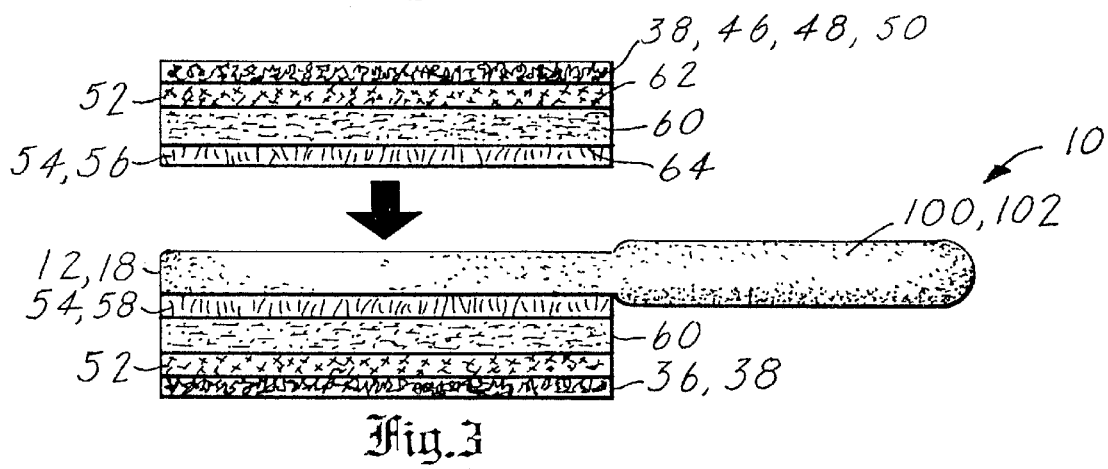
FIG. 3 is a top plan view of an applicator having a rigid substrate to which is attached a flexible substrate. The figure shows one flexible substrate separated from the rigid substrate and a flexible substrate attached to the rigid substrate.

The flexible substrate 60, as shown in FIG. 3, has a first side 62 and a second side 64. To the first side 62 is affixed the water soluble binder material 52 to which is affixed the water-activated color-altering material 38. To the second side 64 of the flexible substrate 60 is affixed an adhesive 54 which is affixed to at least one side 14,16 of the rigid substrate 12.

Figure 4:
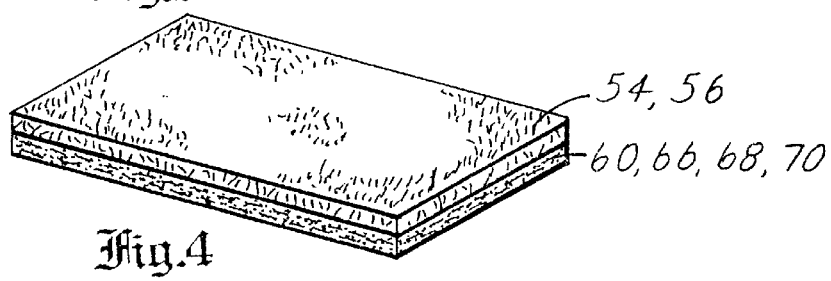
FIG. 4 is a perspective view of a flexible substrate that is constructed of paper, plastic or metal foil.

The adhesive used with the flexible substrate 60 can consist of a contact cement 56 as shown in FIG. 4 or a double-sided adhesive tape 58 as also depicted in FIG. 4. The flexible substrate 60 as shown in FIG. 4 can be comprised of a thin, flat sheet of material formed from paper 66, plastic 68 or a metal foil 70.

Figure 5:
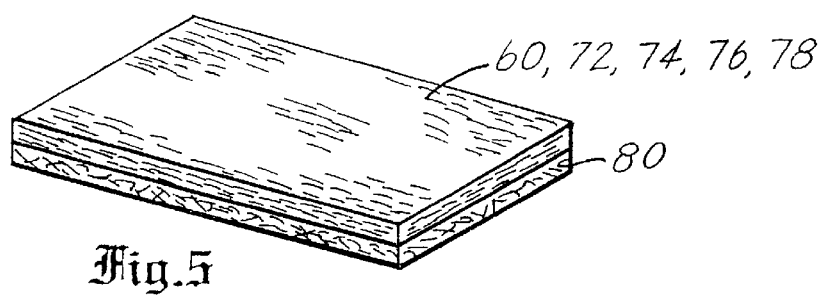
FIG. 5 is a perspective view of a flexible substrate that is constructed of a porous material which includes sponge, fabric or cotton fibers.

Alternatively, as shown in FIG. 5, the substrate 60 can be comprised of a thin, flat sheet of a porous material 72 formed from sponge 74, a fabric 76 or a layer of cotton fibers 78. To facilitate the addition of the water-activated color-altering material 38, a coating of a moisture-impermeable material 80 can be placed between the material 38 and the porous substrate 72 as shown in FIG. 8. In FIG. 3 is shown a flexible substrate 60 detached from the rigid substrate 12 and a second flexible substrate 60 affixed to the rigid substrate 12.

Several binder materials 52 may be used to practice the invention, one such binder material 52 includes a tacky surface. This tacky surface is particularly adapted for accepting a water-activated color-altering material 38 that is comprised of a dry particulate 82 or a powder 84. In this binder, as shown in FIG. 3, the binder material 52 functions as an adhesive 54 to secure the particulate 82 or the powder 84 to the flexible substrate 60. A useful type of binder material is a water-soluable film-forming polymer.

Figure 11:
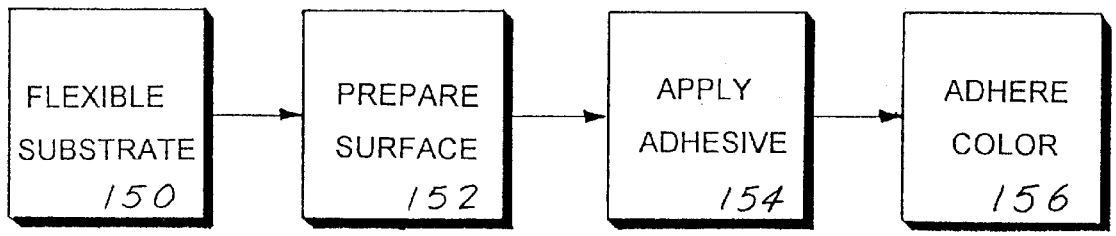
FIG. 11 is a flow diagram showing a sequence of steps of a first process for making the applicator.

In FIG. 11 is a flow chart showing a sequence which is followed to perform a process for affixing the water-activated color-altering material 38 to the flexible substrate 60.

The first block 150 depicts the flexible substrate 60. The second block 152 represents the step of preparing one surface of the substrate 60 for receipt of an adhesive 54. The preparation contemplated for this step involves smoothing and cleaning the surface.

The third block 154 represents the step of applying the adhesive 54 to the one surface of the substrate. This is accomplished by spraying or brushing the adhesive 54 onto the one surface of the substrate 60. The adhesive 54 can include an adhesive composition, such as glue or other similar adherents. The purpose of the adhesive material is to provide a tacky coating on the one portion of the substrate.

The fourth block 156 represents the step of covering the adhesive coating with a dry particulate 82, or a powder 84 which is water soluble and contains a water-activated, color-altering material 38. This step can be accomplished by dusting or otherwise depositing the color-altering material 38 on the adhesive coating.

The color-altering material 38 may be any water-activated colorant that is acceptable for use on hair. The colorant may be permanent 46, semi-permanent 48, demi-permanent 50, and may also be either natural or synthetic. Examples of synthetic colorants useful with the applicator 10 of the invention include, but are not limited to: water-activated HO, D&C, or FD&C colors, nitro dyes such as, nitro derivatives of aminophenols and phenylenediamines; or para-dyes, such as p-phenylene diamine, p-toluenediamine, p-aminophenyldiamine, p-aminophenol and derivatives thereof. Also, indamines and indophenols, and acid and basic colors, such as acid blues, browns, reds, yellows or oranges, and basic blues, greens, yellows, reds, violets, and brown can be used. An exemplary list of cosmetically acceptable hair colorants can be found in the International Cosmetic Ingredient Handbook, Third Edition, Cosmetic Toiletry and Fragrance Association, Washington, D.C., 1995, the contents of which are incorporated herein by reference. Naturally occurring colorants (and their active components) which may be used include, but are not limited to: water activated annatto extracts, saffron (crocin), grape color or grape skin extract (malvidin, delphenidin or cyanidin derivatives), beet extract, (betacyanins or betaxanthins) or henna. Useful colorant components are commercially available, for example, from Jos. H. Lowenstein & sons, Brooklyn, N.Y. In certain cases, particularly when a permanent, or lightening, effect is desired, an oxidizing agent, such as hydrogen peroxide or sodium perborate, may also be employed.

A specific example of components of useful powders (GC Powders, available from Jos. H. Lowenstein & sons) which may be affixed to the rigid substrate 12 or flexible substrate 60, for the production of colors ranging from blond to black, would be: sodium sulfate, sodium perborate, xanthan gum, sodium silicate, silica, sodium lauryl sulfate, and any one or all of the following colorants: 2-amino-6-chloro-4-nitrophenol, p-phenylenediamine sulfate, 4-amino-2-hydroxytoluene sulfate, 2-nitro-p-phenylenediamine sulfate, 2,6-diaminopyridine sulfate, m-aminophenol sulfate, 1,5-naphthalenediol, p-aminophenol sulfate, HC yellow No. 4, 2-chloro-p-phenylenediamine sulfate, 2,5-diaminotoluene sulfate, N,N-Bis(2-hydroxyethyl)-p-phenylenediamine sulfate.

An alternate powder composition is a "bright" powder, also available from Jos. H. Lowenstein & Sons, having the following composition: sodium sulfate, xanthan gum, silica, sodium lauryl sulfate and any one or all of the following colorants: HC yellow no. 4, FD&C blue no. 1, basic blue 9, 2-amino-6-chloro-4-nitrophenol, basic violet 14.

An additional component of the suspension to be applied to the rigid substrate 12 or the flexible substrate 60 may be a hair conditioner. These materials are numerous and well known in the art, and include, for example, jojoba, cetrimonium chloride, quaternium and polyquaternium compounds, dimethicone copolyols, amodimethicone, and the like. An extensive, but not necessarily exhaustive, list of hair conditioners is found in the International Cosmetic Ingredient Handbook, supra, incorporated herein by reference.

Figure 1:
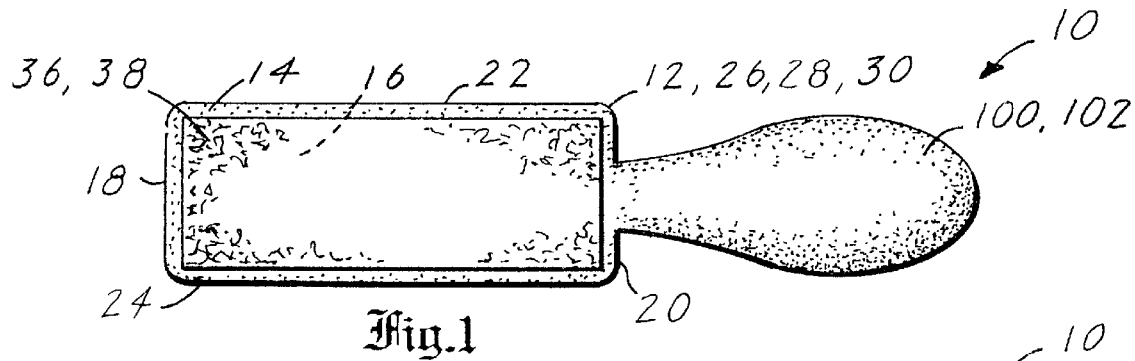
FIG. 1 is an elevational side view of a single-plane applicator having an integral handle.

The tacky coating, and hence the color-altering material, is preferably applied in a substantially geometrical pattern, such as a rectangle as shown in FIG. 1. The coating may also be applied in a plurality of shapes which are contiguous or spaced from one another with regularity or randomness as shown in FIGS. 6 and 7. The coating shapes are designed to provide delivery or transference of the color-altering material 38 to a bundle of hair or fibers in a maximized and efficient manner.

Figure 12:
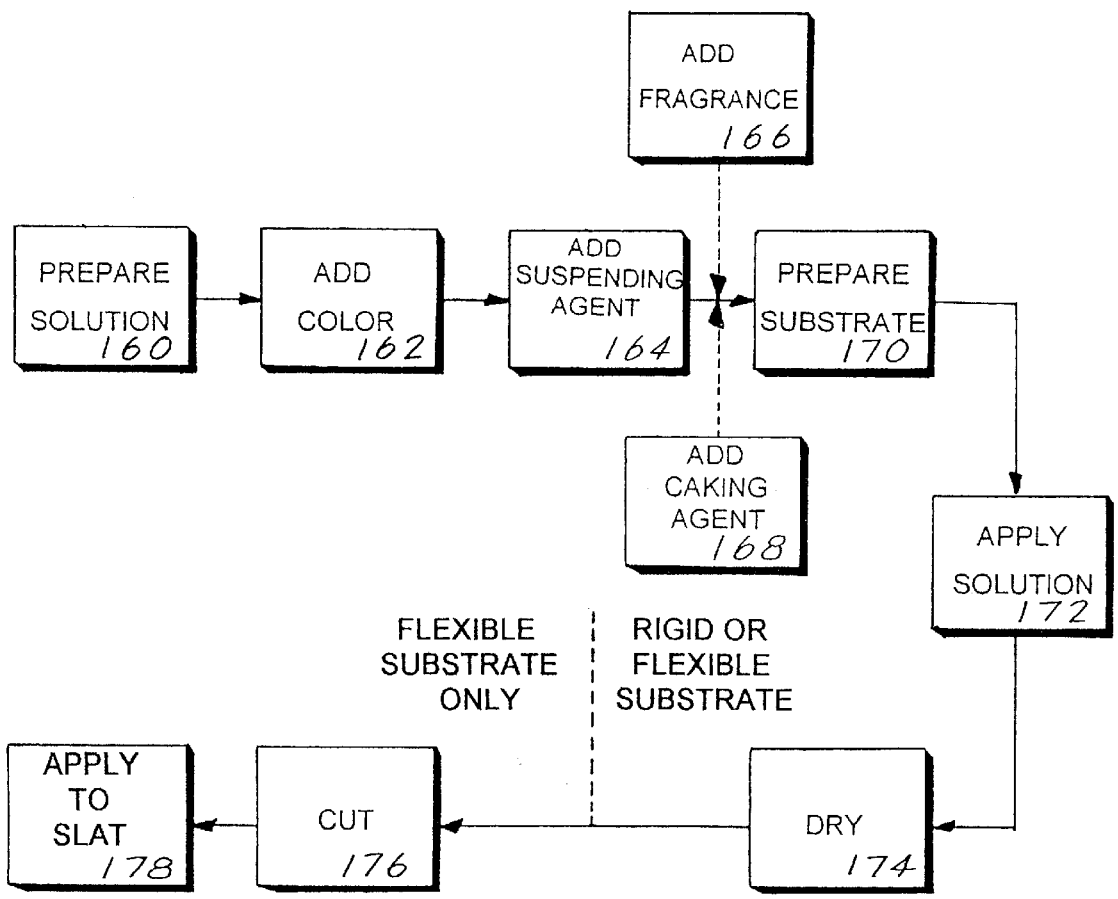
FIG. 12 is a flow diagram showing a sequence of steps of a second process for making the applicator.

FIG. 12 is a block diagram showing the steps contemplated by a second process of the present invention. This process involves initially forming a dye-containing solution, and then applying the solution to a rigid substrate 12 or to a flexible substrate 60.

The first block 160 represents the first step of preparing a solution of a film-forming polymer which acts as the binder material for affixing the color-altering material to the substrate. The film-forming polymer must be soluble in water and alcohol and is chosen such that it possesses a mean molecular weight of between 10,000 and 700,000. Vinyl pyrrolidone polymers, vinyl pyrrolidone co-polymers or a combination thereof are preferred. Alcohols such as methanol, ethanol, 1-propanol, 2-propanol can be used alone or in combination with one another or in combination with a co-solvent. Co-solvents can be various esters, ethers or ketones. Methyl acetate, vinyl acetate, acetone, ethyl methyl ketone, dimethyl ether and isopropyl ether are examples of co-solvents. The polymer solution is preferably prepared as a 4–54 percent wt/wt solution in an alcohol/co-solvent, with a 5–49 percent preferred.

Block 162 represents the second step of adding, under gentle agitation, a desired coloring compound to the polymer-ethanol solution at 11–54 percent of a known weight of the solution. This produces a suspension of coloring compound with a concentration of 10–49 percent.

Block 164 represents the third step of adding a suspending agent to the solution. Typical suspending agents comprise silicone, fumed silica, precipitated silica and the like. The suspending agent facilitates ease of handling during conventional printing processes when a coloring compound is deposited on the rigid substrate 12 or the flexible substrate 60. Preferably, the suspending agent is added at a rate of 0.6–5.0 wt/wt percent of the solution. The suspending agent maintains a homogeneous mixture of the color-altering material 38. The preferred concentration of suspending agent will depend on the type of printing process employed in depositing the solution on the substrate. For example, where the solution is to be deposited on a substrate using flexographic printing method, a 1.1–3.2 wt/wt percent of the color suspension is desirable.

Blocks 166 and 168 represent the fourth and fifth steps of adding fragrances and a caking agent to the solution. The preferred caking agents comprise isopropyl myristate, silicone fluid, diethyl phthalate or petroleum distillates. These caking agents allow a greater deposition of color compound during the printing process. This might be necessary for compounds that produce lighter colors. Where the use of a caking is indicated, a 0.4–2.3 wt/wt percent of a water insoluble/alcohol soluble oil or oily compound is preferably added.

Block 170 depicts the step of preparing the rigid substrate 12 or the flexible substrate 60 for receipt of the solution. In FIG. 12 is shown a step following preparation of the solution, however, it is clear that the step of preparing the rigid substrate 12 or the substrate 60 can be performed before the solution is made.

The rigid substrate 1, to which the solution is to be applied can be made from a plastic material 26, a wood 28 or a metal 30. The flexible substrate as shown in FIG. 4, can be made from a thin, flat sheet of a material formed from paper 66, plastic 68 or a metal foil 70. Additionally, the flexible substrate 60, as shown in FIG. 5, can also be made from a porous material which includes a sponge 74, a fabric 76 or cotton 78.

Preparation of the rigid or flexible substrates includes one or more steps of smoothing, cleaning and drying the portion onto which the solution is to be applied. Further, the step of preparing the substrates can include the application of a moisture impermeable coating to the surface of the substrates on which the solution is to be applied. Such coatings include wax, saran, polyester, ultra violet cured coatings and latex coatings. These moisture impermeable coatings prevent the coloring compound from passing through the substrates and staining the user's hands or fingers. For the flexible substrate 60, latex based or latex impregnated paper stocks can be employed as well as commercial "wet strength" paper stocks.

In block 172 of FIG. 12, the process utilizes the further step of applying the color-altering solution to the rigid substrate 12 or the flexible substrate 60 via conventional printing methods, such as flexographic printing, gravure, silkscreen or offset printing. After the solution is applied to the substrates, they are immediately passed through a gas-fired forced-air print dryer, as shown in block 174, at which time the process for the rigid substrate is concluded as indicated in FIG. 12.

One method of applying the solution to the flexible substrate is by the wet offset process, which utilizes a flexographic apparatus. The solution is printed on the first side 62 of the substrate 60 in the form of either a single strip as shown in FIGS. 3, 4 and 5 or segmented strips as shown in FIGS. 6 and 7. Once the strip of coloring compound is applied, the substrate is immediately passed through the gas-fired forced-air print drier as shown in block 174. After drying the web is cut into individual pieces, as shown in block 176, for application to the rigid substrate 12 as shown in block 178 and in FIGS. 1 and 3 or to the pair of rigid substrates 12,110 as shown in FIGS. 9 and 10.

The means 100 for grasping and manipulating the rigid substrate 12 is shown in FIGS. 1–3 and 6–10. In FIG. 1 is shown a handle 102 having an elliptical shape and that integrally extends from the inner edge 20 of the substrate 12. In FIG. 2 is shown a handle 102 having a slot 104 dimensioned to receive and retain the inner edge 20 of the rigid substrate 12. The slot 104 can either be retained by friction or an adhesive can be applied. In FIGS. 3, 6 and 8 is shown an elongated round handle 102. The elongated round handle 102 is particularly adaptable for including a plurality of teeth 106 that extend laterally from an edge of said handle 102. In FIG. 7 is shown a pair of finger slots 108 that extend along the outer edge 18 and inner edge 20 of the rigid substrate 12.

The use of the applicator 10 preferably involves wetting the bundle of hair or fibers, which have been identified for coloring, and then interposing the applicator 10 between the user's hand and the hair or fibers to be colored. The user then either presses the applicator against the wet hair and contemporaneously moves the applicator relative to the hair or fibers with a wiping motion, or if using the applicator 10 as shown in FIGS. 9 and 10, wraps the applicator about the hair or fibers while firmly squeezing the hair or fibers while firmly squeezing the hair or fibers within the encircling applicator.

Use of the applicator 10 can also be achieved by first wetting the applicator itself, as for example with a mist of water or steam, and when wiping or squeezing it against hair or fibers. The initial dampening of the applicator, or the contact of a dry applicator with wet hair, causes the water-activated dye particles to mix with the water for form a dye-containing solution on the surface of the applicator.

The squeezing and/or wiping motion of the applicator relative to the hair or fibers enables the dye-containing coloring compound to be transferred to the hair or fibers.

The applicator and method for making such, as described above in connection with the present invention, involves the deposition of the color-altering compound solution on the applicator by processes similar to those depicted in FIGS. 11 and 12.

While the invention has been described in complete detail and pictorially shown in the accompanying drawings it is not to be limited to such details, since many changes and modifications may be made in the invention without departing from the spirit and scope thereof. For example, the flexible substrate 60 made from a thin sheet of paper 66, plastic 68 or a metal foil can be rolled onto a spindle which is rotatably attached to a dispenser having a cutting edge. The flexible substrate 60 can then be dispensed to a required length, cut and attached to one of the rigid substrates described supra. Hence, it is described to cover any and all modifications and forms which may come within the language and scope of the appended claims.

I claim:

1. An applicator for transferring color-altering material to strands of hair or fibers, said applicator comprising
   a) a rigid substrate having a first side, a second side, an outer edge, an inner edge, an upper edge and a lower edge,
   b) a flexible substrate having a first side and a second side, wherein to the first side is affixed a water soluble binder material to which is affixed said water-activated color-altering material, and to the second side of said flexible substrate is affixed an adhesive which is affixed to at least one side of said rigid substrate,
   c) means for grasping and manipulating said rigid substrate.

2. The applicator as specified in claim 1 wherein said rigid substrate comprises a plastic material.

3. The applicator as specified in claim 1 wherein said rigid substrate comprises a wood.

4. The applicator as specified in claim 1 wherein said rigid substrate comprises a metal.

5. The applicator as specified in claim 1 wherein said water-activated color-altering material comprises at least one of a hair color, a bleaching compound, and a conditioning agent.

6. The applicator as specified in claim 1 wherein said color-altering material is selected from a group comprising a permanent, semi-permanent or demi-permanent hair coloring.

7. The applicator as specified in claim 1 wherein said means for affixing said water-activated color-altering material comprises a binder material incorporating an adhesive which allows said binder material to be directly affixed to at least one side of said rigid substrate, and said color-altering material to be directly affixed to said binder material, wherein said binder material, said adhesive and said color-altering material are water soluble.

8. The applicator as specified in claim 7 wherein said color-altering material comprises a dry particulate which functions as an adhesive to secure said particulate.

9. The applicator as specified in claim 1 wherein said adhesive comprises a contact cement.

10. The applicator as specified in claim 1 wherein said adhesive comprises a double-sided adhesive tape.

11. The applicator as specified in claim 1 wherein said flexible substrate comprises a thin, flat sheet of material selected from a group comprising paper, plastic or a metal foil.

12. The applicator as specified in claim 1 wherein said flexible substrate comprises a thin, flat sheet of a porous material selected from a group comprising sponge fibers, fabric or a layer of cotton fibers.

13. The applicator as specified in claim 12 wherein said porous substrate material includes a coating of moisture-impermeable material between said water-activated color-altering material and said porous substrate.

14. The applicator as specified in claim 1 wherein said binder material includes a tacky surface and said water-activated color-altering material comprises a dry particulate, wherein said binder material functions as an adhesive to secure said particulate to said flexible substrate.

15. The applicator as specified in claim 14 wherein said binder material comprises a solution of a film-forming polymer that is soluble in water and alcohol and has a mean molecular weight of between 10,000 and 700,000.

16. The applicator as specified in claim 15 wherein said film-forming polymer is selected from a group comprising vinyl pyrrolidone polymers, vinyl pyrrolidone copolymers, or a combination thereof.

17. The applicator as specified in claim 16 wherein said film-forming polymer affixes to both said water-activated color-altering material and said flexible substrate, said polymer being water soluble, and therefore able to release said water-activated color-altering material when contacted with water.

18. The applicator as specified in claim 15 wherein said alcohol comprises at least one of methanol, ethanol, 1-propanol, or 2-propanol.

19. The applicator as specified in claim 18 wherein the alcohol is combined with a co-solvent which comprises at least one ester, ether or ketone.

20. The applicator as specified in claim 15 wherein said film-forming polymer is prepared as a 4–54 percent wt/wt solution in alcohol/co-solvent.

21. The applicator as specified in claim 1 wherein said means for grasping said rigid substrate comprises a handle that extends from the inner edge of said rigid substrate.

22. The applicator as specified in claim 21 wherein said handle is integral with the inner edge of said rigid substrate.

23. The applicator as specified in claim 21 wherein said handle further comprises a slot dimensioned to receive and retain the inner edge of said rigid substrate.

24. The applicator as specified in claim 21 wherein said handle further comprise a plurality of teeth that extend laterally from an edge of said handle.

25. The applicator as specified in claim 1 wherein said means for grasping and manipulating said rigid substrate comprises a finger slot that extends along the outer edge and inner edge of said rigid substrate.

26. The applicator as specified in claim 1 wherein said rigid substrate comprises an elongated narrow structure having a front section and a rear section, wherein around the front section is attached a bundle of soft fibers to which is affixed said water-activated color-altering material, and wherein the rear section of said structure extending from said bundle of soft fibers, functions as a handle which provides the means by which said applicator is grasped and manipulated during usage.

27. The applicator as specified in claim 26 wherein said bundle of soft fibers comprises cotton fibers.

28. The applicator as specified in claim 26 wherein said bundle of soft fibers comprises sponge fibers.

29. The applicator as specified in claim 1 wherein said rigid substrate further comprises a second rigid substrate having similar dimensions as said rigid substrate and having a first side, a second side, an outer edge, an inner edge, an upper edge and a lower edge, wherein the upper edge of said second rigid substrate is attached, by means of a living hinge, to the upper edge of said rigid substrate, wherein to at least one of the first sides of said rigid substrate or said second rigid substrate is affixed said water-activated color-altering material, wherein the second sides of said rigid substrate and said second rigid substrate provide the means by which said applicator is grasped and manipulated during usage.

30. A method of making an applicator for coloring hair or fibers, comprising the steps of:
   a) providing a rigid substrate having a first side and a second side,
   b) affixing a binder material consisting of a tacky substance to the at least one side of said rigid substrate,
   c) affixing a water-activated color-altering material to said binder material,
   d) drying said rigid substrate, and
   e) grasping said rigid substrate and wiping the at least one side having said water-activated color-altering material against said hair or fibers.

31. The method as specified in claim 30 including the further step, before affixing said water-activated color-altering material on said substrate, of preparing a solution of water-soluble film forming polymer in alcohol, where the polymer possesses a mean molecular weight of between 10,000 and 700,000.

32. The method as specified in claim 31 further including the step of adding the water-activated color-altering material to said solution.

33. The method as specified in claim 32 further including the step of adding to said solution a suspending agent.

34. The method as specified in claim 33 wherein said suspending agent comprises silicone, fumed silica, or a precipitated silica.

35. The method as specified in claim 33 further including the step of adding to said solution a caking agent.

36. The method as specified in claim 35 wherein said caking agent comprises isopropyl myristate, silicone fluid, diethyl phthalate or petroleum distillates.

37. The method as specified in claim 33 further including the step of adding to said solution a fragrance.

38. The method as specified in claim 30 wherein the step of affixing said water-activated color-altering material comprises printing said material on at least one side of said rigid substrate.

39. A method for coloring hair, comprising the steps of:
   a) wet either,
      (1) the hair to be colored;
      (2) a rigid substrate; having a first side and a second side, wherein a water-activated color-altering material is affixed to at least one side of said rigid substrate, or
      (3) both hair and said rigid substrate;
   b) contact the wet hair with a portion of said rigid substrate to which the dye is affixed, and
   c) maintain contact between said rigid substrate and the hair for a period of time sufficient to transfer said hair dye form said substrate to the wet hair.

40. The method as specified in claim 39 wherein said step of contacting the wet hair comprises moving said rigid substrate relative to said hair so that the transfer of hair dye to said hair can be effected.

* * * * *